United States Patent [19]

Glumac

[11] 4,422,461
[45] Dec. 27, 1983

[54] ELECTRODE

[76] Inventor: George Glumac, RR 2, Box 252G, Conifer, Colo. 80433

[21] Appl. No.: 292,218

[22] Filed: Aug. 12, 1981

[51] Int. Cl.³ .............................................. A61N 1/04
[52] U.S. Cl. .................................... 128/798; 128/802
[58] Field of Search ................................ 128/639–641, 128/798, 802, 803, 784

[56] References Cited

U.S. PATENT DOCUMENTS

| | | | |
|---|---|---|---|
| 1,989,282 | 1/1935 | Kimble et al. | 128/798 |
| 3,606,881 | 9/1971 | Woodson | 128/641 |
| 3,817,252 | 6/1974 | Maurer | 128/798 |
| 3,977,392 | 8/1976 | Manley | 128/641 |
| 3,994,302 | 11/1976 | Brennen | 128/784 |
| 4,092,985 | 6/1978 | Kaufman | 128/798 |
| 4,207,904 | 6/1980 | Greene | 128/798 |
| 4,300,575 | 11/1981 | Wilson | 128/798 |

FOREIGN PATENT DOCUMENTS

| | | | |
|---|---|---|---|
| 2735050 | 2/1979 | Fed. Rep. of Germany | 128/640 |
| 787477 | 9/1935 | France | 128/798 |

Primary Examiner—Lee S. Cohen
Attorney, Agent, or Firm—Hugh D. Jaeger

[57] ABSTRACT

Electrode such as a post-operative electrode including a combination of plastic foam with an adhesive layer, an electrical communication conductor member such as a wire or a thin foil member such as aluminum or silver, a thin polycarbonate member or members loaded with a conducting material such as carbon, a conductive medium, and a liner member. The foil member and polycarbonate member are thin providing for flexibility and low profile, and are substantially of like identical surface area. The conductive member can be either karaya, electrode gel, ionic polymer, or other like medium. The electrode is very flexible and very conforming to the surface of the skin of the individual user.

18 Claims, 2 Drawing Figures

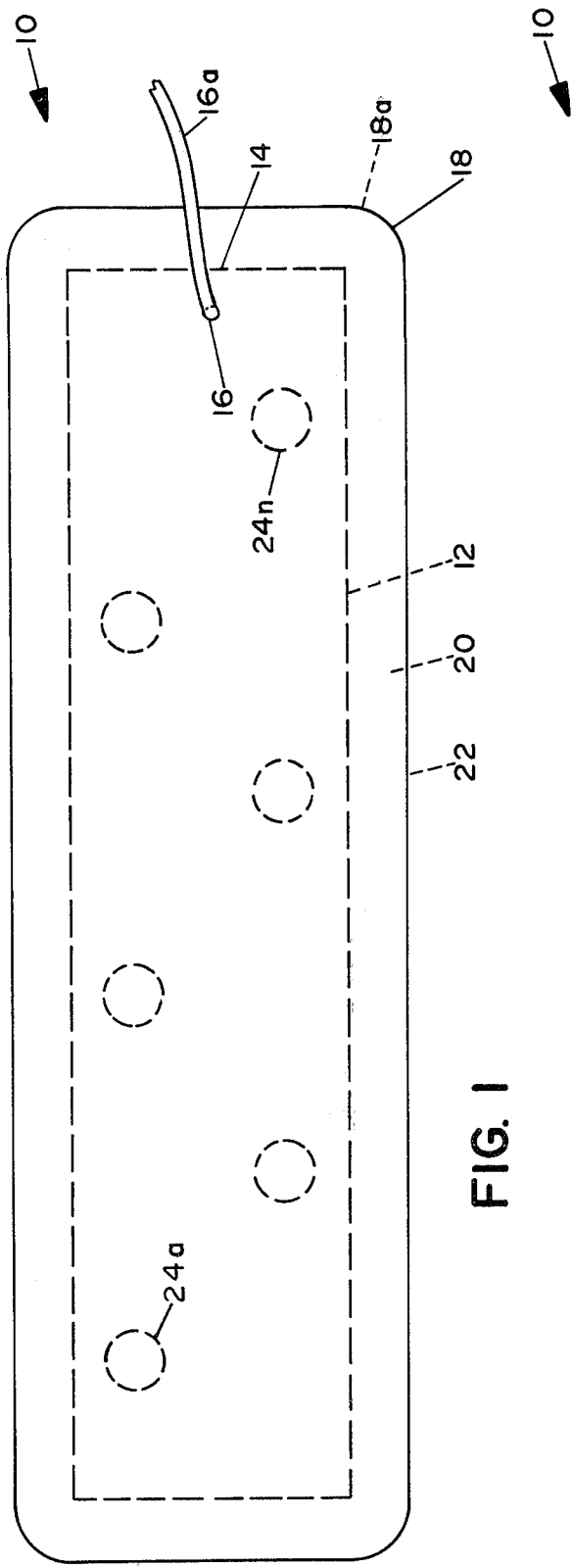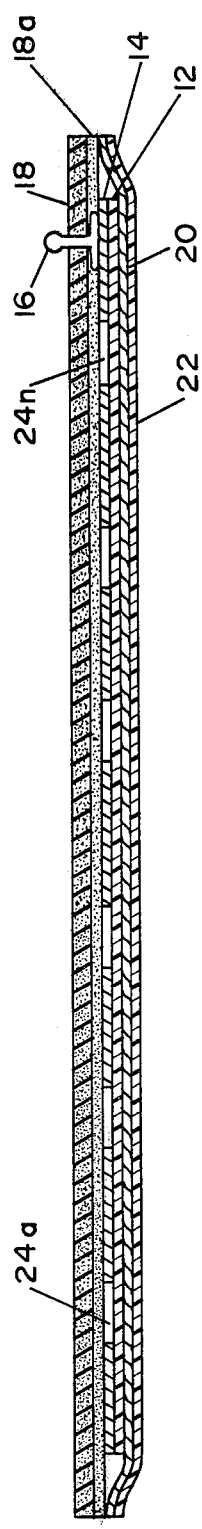
FIG. 1
FIG. 2

ELECTRODE

BACKGROUND OF THE INVENTION

1. Field of the Invention

The present invention relates to surgery and, more particularly, pertains to an electrode for acute, chronic, and post-operative conditions to alleviate pain and enhance motor control of an individual.

2. Description of the Prior Art

The prior art electrodes have failed to meet the medical needs of individuals in not providing a stimulating electrode which provides for electrical distribution of current as well as a personal comfort factor of distribution of electrical current.

The prior art stimulating electrodes have been rather complex, bulky, molded, non-flexible devices which have been less than comfortable for use by the individual patient, and in addition have provided less than equal current distribution resulting in hot or burn spots on the individual's skin from the electrode stimulation.

The prior art electrodes have been large rubber-type devices being non-flexible and having a high profile, especially noticeable under an individual's clothing, and have detracted from the medicinal purpose and benefit of the stimulating electrode. Due to the non-flexibility and bulkiness, the stimulation electrodes tend to pull away from the skin requiring adhesives of maximum adherence, thereby causing irritation and a non-comfort factor to the individual's skin. To further compound the problem, the electrodes which tend to pull away and lift from the skin inherently contribute to the condition by increasing the current densities at higher densities at the individual skin touching points, causing what is known in the art as hot spots.

The prior art electrodes have failed to meet the needs of the post-operative, chronic and acute pain applications. The prior art electrodes are usually bulky, molded silicone rubber loaded with a carbon resulting in an electrode which is thicker, less flexible, and of a high impedance. In addition, the potential distribution of the electrode from the conductor drops off as a function of distance square from the point of contact to the periphery of the electrode.

The present invention overcomes the disadvantages of the prior art electrodes by providing an electrode which is low profile, includes a backing of adhesive plastic material providing for adhesion to the surface of the individual's skin, a combination of conductive film material and metallized backing, is very flexible and very low profile and the metalized backing provides a finite impedance for equalized current distribution. The equalized current distribution also provides for least amount of energy usage.

SUMMARY OF THE INVENTION

The general purpose of the present invention is to provide a post-operative electrode which is very thin and very flexible, very low profile, and readily manufacturable for low cost to the individual patient user which is a prime requirement in today's world of rising medical and rising medical treatment costs. More importantly, though, the electrode is very flexible and very low profile so as not to be bulky or cumbersome to the individual, thereby requiring less conductive medium as the electrode adheres with relative ease to the skin of the individual user.

According to one preferred embodiment of the present invention, there is provided an electrode including a plurality of layers, the layers including a layer of covering material such as plastic foam with an adhesive layer disposed on one side thereof, a layer of metallic foil material such as aluminum or silver disposed over a layer of conductive polycarbonate film, the metallic foil and polycarbonate film being substantially the same geometrical configuration and slightly smaller in geometrical configuration than that of the layer of plastic foam, a plurality of holes spaced throughout the metallic foil, and an electrical snap conductor engaged to the metallic foil at one end thereof and protruding through the plastic foam layer and having a wire connected thereto for connection to a suitable electrical stimulator or sensing device, a layer of conductive medium such as ionic polymer, pellon loaded with electrode conductive fluid or gel, or Karaya, and a liner of plastic of the same geometrical configuration as the layer of plastic foam whereby the randomly spaced holes secure the plastic foam layer to the polycarbonate layer with the metal film disposed therebetween, the metallic foil provides for electrical communication with the snap electrical connector providing for placement of the same at either end of the electrode with equalized current distribution, the combination of the polycarbonate layer and metallic foil layer provides for equalized current distribution and an equalized impedance for either the electrical stimulator or electrical sensor connected thereto through said electrical snap connector and said wire, and the liner retains the conductive medium sterile and sealed, thereby providing a very thin, very flexible and very low profile electrode for either stimulation or sensing.

A significant aspect and feature of the present invention is an electrode for either stimulation or sensing which is very thin, very flexible, very low profile and very automatable from a manufacturing process standpoint, thereby providing a medical-surgical product to the patient at a reasonable cost of treatment. More importantly though, the electrode is very thin and very flexible, conforming to the deformity in one's individual skin during movement and muscular action, and also has a very low profile for placement under articles of clothing.

Another significant aspect and feature of the present invention is an electrode which uses a combination of a polycarbonate film material and a metallic foil, thereby providing for equalized current distribution and homogeneous impedance over the stimulating surface of the electrode. The combination of the metallic foil and polycarbonate film which can either be laminated together or vapor desposited on the polycarbonate film provides for placement of an electrical connector to a wire anywhere on the metallic film, thereby providing for equalized current distribution.

A further significant aspect and feature of the present invention is an electrode which is very suitable as a post-operative electrode in a rectangular configuration. While the electrode can assume any predetermined geometrical configuration such as a circle, ovoid, square, rectangle, etc., the particular disclosure here in this patent is by way of example and for purposes of illustration only and not to be construed as limiting of the present invention.

An additional significant aspect and feature of the present invention is to provide an electrode which is very flexible and very conforming to the surface of the skin of an individual's body. The combination of the relatively high impedance film, such as the polycarbonate film, and the low impedance foil material, such as the silver, adheres to each other such as by metalizing or laminating, provides a very unique electrode. The distributed impedance provides for equalized current distribution thereby providing for least amount of current usuage.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a top view of an electrode, the present invention; and,

FIG. 2 illustrated a cross-sectional view of the electrode of FIG. 1.

DESCRIPTION OF THE PREFERRED EMBODIMENTS

FIG. 1, which illustrates a top view of an electrode 10, shows an electrode 10 having a combination of layers of film material for stimulation at a predetermined location of an individual. The electrode 10 includes a high-impedance conductive film 12 as also illustrated in FIG. 2 which can include polyethylene material which can be loaded with conductive carbon by way of example and for purposes of illustration only and not to be construed as limiting of the present invention. Other materials can include polycarbonate, urethane, silastic, vinyl, or any other type of material which can be produced in a film form, made conductive, and receive a finite layer 14 of low-impedance metalization. In this particular instance, the high-impedance conductive film 12 is a Kimberly-Clark polycarbonate film loaded with carbon thereby making the film 12 conductive and having a thickness preferably of 0.5 mil but in the range of 0.1 to 5 mils.

A finite layer 14 of low-impedance conductive material, preferably a metalized layer of aluminum, silver or other conductive material, by way of example and for purposes of illustration can be metalized, vapor deposited, laminated, photo etched or other process of film or foil deposition or limitation in a predetermined geometrical configuration to the film material 12. The foil material 14 is in electrical and mechanical contact to the high-impedance conductive film 12, and is positioned on an upper side of the high-impedance conductive film 12 as illustrated in FIG. 2.

A snap connector 16 positions over the metalized film 14 in mechanical and electrical contact therewith at any position and in the example, at one end as electrical distribution is equalized by the foil member 14.

A plastic foam or film 18 with a thin adhesive layer 18a where the plastic foam is in the range of 1 to 20 mils thickness and the adhesive layer is a fraction of a millimeter secured to the top of a conductive film 12 and metallic film 14, and includes a larger surface area than the conductive film 12 metalized foil film as also illustrated in FIG. 2. A conductive medium 20 having a geometrical configuration to that of layer 18 overlaps with a surface area larger than the conductive film 12 and the metal film 14 and like surface area to the under side of the adhesive layer 18a of the foam material 18. The foam or film material 18 also secures to the top edge portion of the conductive medium 20 and includes a surface area and a surface configuration substantially identical to that of the plastic film layer 18. In this instance, the conductive medium is Karaya. A plastic liner 22 is provided over the bottom of the karaya for sterility and protection of the conductive medium surface. Ionic polymers, pellons with gel or fluid can also be utilized as conductive mediums in lieu of the karaya. A plurality of spaced or randomly spaced holes 24a-24n are provided in the metal foil layer 14 for securing the conductive film 12 to the adhesive layer 18a through the randomly spaced holes 24a-24n. A wire 16a extends outwardly from electrical snap 16.

FIG. 2 illustrates a cross-sectional view of the electrode 10 of FIG. 1 including the layers of conductive film 12, metallic film 14, snap connector 16, top foam or film 18 with adhesive 18a, and bottom conductive medium 20 with plastic liner 22 which is removed prior to use. The metal foil 14 has an impedance of a few ohms at the most while the conductive film 12 has a relatively high impedance, where relatively high impedance is fifty to one hundred ohms by way of example and for purposes of illustration only and not to be construed as limiting of the present invention where the fifty to one hundred ohms of the film 12 is considered to be relatively high with respect to the metal foil 14. The bottom conductive medium can also be such material so as to have suspending or fluid retaining capabilites, and can include such materials such as pellon with a conductive fluid or gel in lieu of Karaya, or an ionic polymer.

MODE OF OPERATION

The electrode 10 of the present invention is utilized in a post-operative nature usually in pairs where the electrodes are utilized by removing the liner 22 and positioning the electrodes at the desired point of stimulation. Subsequently the wires are connected to a suitable stimulation device such as a TENS unit, and stimulation is commenced by prescribed settings by a physician or surgeon. The electrodes, for example, might be positioned on either side of a surgical incision on an individual's body to alleviate pain and enhance healing about that incision or incisions.

In the event where the electrode 10 is used in a sensing mode of operation, any number of the electrodes 10, whether the electrode 10 be of a rectangular configuration or other geometrical configuration, are positioned at predetermined sensing sites and appropriately connected to sensing equipment such as EKG, etc. Usage is likewise where the liner 22 is removed from the electrode prior to positioning on an individual's skin.

The electrode is packaged in a sterile package known in the art and protected by the liner 22. Prior to usage, the electrode is removed from the package, the liner is peeled away, and the electrode is applied to the skin and connected to the TENS unit for usuage by way of wire 16a. The liner 22 protects the adhesive 18 while a sterile wrap is provided around the entire electrode 10 for sterility.

Various modifications can be made to the present invention without departing from the apparent scope thereof. The holes can be spaced either in a predetermined order or randomly, and are of such a size to securing the adhesive layer through the metal foil to the conductive film layer. The size of the holes, whether large or small, has no effect of the current distriubution over the metal foil material as the current flows uniformly along the metal foil. The holes would usually be prepunched through the foil and could comprise a plurality of small holes with respect to the electrode size which might at a glance take a random configuration on the metal material.

What is claimed is:

1. Electrode comprising:
   a. a layer of high-impedance carbon-loaded polycarbonate film material of a thickness of 0.1–5 mils;
   b. a metalized layer of low-impedance metallic foil material vapor desposited over said film material in a like geometrical configuration as said film material;
   c. a layer of plastic covering material with adhesive securing means disposed on a side of said foil material opposite said film material, said plastic covering material slightly larger than said film material and said foil material, and said securing means joining said film material, said foil material, and said plastic covering material together;
   d. a conductive medium layer disposed on a side of said film material opposite said foil material and substantially covering said film material; and,
   e. snap means for electrically connecting to said electrode in electrical and mechanical connection to said foil material whereby said electrode maintains maximum flexibility and minimum profile over skin of an individual.

2. Electrode of claim 1 wherein said metallic foil material is aluminum foil.

3. Electrode of claim 1 wherein said metallic foil material is silver.

4. Electrode of claim 1 wherein said covering material is plastic foam.

5. Electrode of claim 1 wherein said conductive medium in Karaya.

6. Electrode of claim 1 wherein said conductive medium is ionic polymer.

7. Electrode of claim 6 wherein said ionic polymer is equal in shape to said layer of covering material.

8. Electrode of claim 1 wherein said conductive medium is pellon material engaged to said securing means and conductive electrode gel disposed therein.

9. Electrode of claim 1 wherein said layer of covering material and conductive medium layer are slightly larger in size than said film material and foil material.

10. Electrode of claim 1 comprising a liner layer disposed over said conductive medium.

11. Electrode of claim 1 comprising a plurality of small spaced holes in said foil material whereby said holes provide for securing said layer of covering material to said film material.

12. Electrode of claim 1 wherein said snap means is a snap electrical connector mechanically and electrically engaged to said foil material and through said layer of covering material.

13. Electrode of claim 1 wherein said electrode is of a rectangular geometrical configuration for post-operative usage.

14. In combination, an electrode, said electrode comprising:
   a. a layer of carbon loaded, polycarbonate conductive film material of a thickness of 0.1–5 mils having a relatively high impedance;
   b. a layer of metallic foil material having a relatively low impedance, said foil material in electrical and mechanical contact with said film material; and,
   c. snap electrical connecting means engaged and in contact with said foil material for transferring electrical energy to said film material whereby said combination of film material and said foil material provides maximum flexibility and minimum profile of said electrode.

15. Electrode comprising:
   a. a layer of high-impedance carbon-loaded synthetic film material of a thickness in the range of 0.1–5 mils;
   b. a layer of aluminum metallic foil material electrodeposited over said film material and in electrical and mechanical contact therewith and substantially geometrically configured as said film material and including a plurality of small spaced holes;
   c. a layer of covering material with securing means on one side thereof, said material slightly larger than said film material and said foil material, and said securing means joining said film material, said foil material, and said covering material together through said holes and disposed on a side of said foil material opposite said film material;
   d. a conductive medium Karaya layer disposed on a side of said film material opposite said foil material and substantially covering said film material; and,
   e. snap means for electrically connecting to said foil material at one end thereof whereby said electrode maintains maximum flexibility and minimum profile and provides for least energy usage at point of stimulation.

16. Electrode of claim 15 wherein said synthetic film material is vinyl.

17. Electrode of claim 15 wherein said synthetic film material is urethane.

18. Electrode of claim 15 wherein said synthetic film material is polycarbonate.

* * * * *